United States Patent [19]

Knuuttila et al.

[11] Patent Number: 5,177,291
[45] Date of Patent: Jan. 5, 1993

[54] METATHESIS PROCESS FOR OLEFINES AND A CATALYST TO BE APPLIED THEREIN

[75] Inventors: Pekka Knuuttila; Jukka Hietala; Anja Linna, all of Porvoo, Finland

[73] Assignee: Neste Oy, Finland

[21] Appl. No.: 798,508

[22] Filed: Nov. 26, 1991

[30] Foreign Application Priority Data

May 12, 1990 [FI] Finland .................... 906020

[51] Int. Cl.⁵ .................................. C07C 6/04
[52] U.S. Cl. ............................ 585/646; 585/644; 502/254; 502/309
[58] Field of Search ............ 585/643, 644, 646, 324

[56] References Cited

U.S. PATENT DOCUMENTS

| | | |
|---|---|---|
| 3,431,316 | 3/1969 | Banks .................... 585/644 |
| 3,660,517 | 5/1972 | Reusser et al. .................... 585/644 |
| 3,792,106 | 2/1974 | Regier .................... 585/646 |
| 3,865,751 | 2/1975 | Banks et al. .................... 585/646 |
| 4,490,477 | 12/1984 | Hobbs .................... 585/646 |
| 4,596,786 | 6/1986 | Kukes et al. .................... 585/646 |
| 4,609,769 | 9/1986 | Kukes et al. .................... 585/643 |

Primary Examiner—Anthony McFarlane
Attorney, Agent, or Firm—Steinberg & Raskin

[57] ABSTRACT

A metathesis process of the conversion of olefines, in which at least one olefine is brought into contact with a solid catalyst system comprising on a solid silica carrier 0.1–40% by weight of a tungsten compound under reaction conditions such that the catalyst system converts the olefine into olefines having a different molecular weight. In the process a magnesium oxide or titanium oxide containing co-gel prepared by means of a co-gelling system is used as the silica carrier.

11 Claims, No Drawings

METATHESIS PROCESS FOR OLEFINES AND A CATALYST TO BE APPLIED THEREIN

BACKGROUND OF THE INVENTION

The invention relates to a metathesis process for the conversion of olefines as well as a catalyst to be applied therein.

The metathesis or disproportionation of olefines refers to a reaction, in which one or more olefines are converted into olefines having a different molecular weight. The olefine may be disproportionated with itself into olefines having a higher molecular weight and into olefines having a lower molecular weight. In this case, the reaction may be called a "self-disproportionation". Two different olefines can also be converted into other olefines by means of the metathesis reaction.

In order to function, the metathesis reactions of olefines require a catalyst system, which includes a transition metal compound, often a cocatalyst, and sometimes also a compound which acts as a promoter. Catalyst systems based on tungsten and molybdenum are especially efficient. Such catalysts generally comprise a tungsten or molybdenum oxide on an inorganic carrier, such as silica or alumina.

It is known to add to such catalysts different substances which act as promoters. Thus, for example according to the EP Publication No. 152112, a titanium oxide or titanium-containing substances are added to the surface of the catalyst as a promoter. The U.S. Pat. No. 4,559,320, describes the use of a tungsten catalyst on a silica carrier, to which catalyst is also added a magnesium oxide.

SUMMARY OF THE INVENTION

In accordance with the present invention, it has surprisingly bee observed that the activity of tungsten catalysts that contain magnesium oxide or titanium oxide in the metathesis process of olefines can be considerably improved by the use of silica co-gel as a carrier, in which the silica is gelled together with a magnesium oxide or titanium oxide before the addition of the tungsten.

It is accordingly a primary object of the present invention to provide a metathesis process for the conversion of olefines wherein the reaction proceeds in an extremely pure manner without acid catalytic side reactions.

It is a further object of the present invention to provide improved catalyst systems for the metathesis process of conversion of olefines.

Other objects and advantages of the present invention will be apparent from a further reading of the specification and of the appended claims.

In accordance with an additional feature of the invention, improvements are also achieved in the activity, if the catalyst in the metathesis process of olefines is fitted into a reactor in a certain manner.

In the catalyst to be used in the process of the invention, the co-gel to be used as a carrier may be prepared from solutions of silicate and magnesium or titanium compounds. The sodium silicate solution is thus reacted with a suitable magnesium salt, e.g. with magnesium oxide, magnesium hydroxide, magnesium nitrate, magnesium sulphate, magnesium acetate, the pH-value being over 8, whereby co-gels are obtained, whose general properties depend on the $SiO_2/Mg$ stoichiometry and the processing conditions.

The magnesium salts may alternatively be mixed with hydrosols, which have been obtained by acidating sodium silicate solutions when the pH-value is less than 4, whereby silica/magnesia co-gels are obtained, whose general properties depend on the stoichiometric conditions used, the pH-value, the reaction time and the temperature. The testing and adjustment of these parameters is apparent to those skilled in the art. The hydrogel obtained in this way is washed and dried. Silica-titanium oxide co-gels are prepared to a similar manner.

The co-gels obtained are advantageously ion exchanged by means of any acid or ammonium salt for removing the alkali metal cations suitable for the ion exchange. In addition, the co-gels obtained can be activated before use by heating them to a temperature of over 200° C. to a water content of about 10%, whereby at least the surface layer of the co-gel changes into an acid form.

In the inventive process, such co-gels can be preferably used as a carrier of the catalyst, in which the Si/Mg ratio is in the range 10/1–10000/1 or the Si/Ti ratio is in the range of 10/1–10000/1.

The tungsten catalyst to be used in the inventive process is prepared from co-gels prepared in the manner described above by adding thereto a tungsten oxide in any manner desired. The tungsten may be added either directly as an oxide or as a precursor. In the last-mentioned case, the oxide precursor is changed into an oxide form by calcination. Suitable oxides or precursors are tungsten compounds, which can be changed into an oxide form under the calcination conditions. Examples of suitable tungsten compounds include oxides, halides, sulphides, sulphates, nitrates, acetates and their mixtures.

Examples of suitable tungsten compounds thus include tungsten pentachloride, tungsten dichloride, tungsten tetrachloride, tungsten hexafluoride, tungsten trioxide, tungsten dioxychloride, tungsten trisulphide, metatungsten acid, orthotungsten acid, ammonium phosphotungstenite and ammonium metatungstenite.

The quantity of the tungsten oxide or tungsten precursor in the co-gel carrier may vary from 0.1% by weight of tungsten oxide to 40% by weight. A suitable quantity is generally within the range 2–20% by weight.

The tungsten oxide or precursor may be added to the co-gel carrier either by dry mixing or by absorption from a solution. In the latter case, the co-gel carrier is treated with a tungsten compound solution, and the extra solution is then removed. Alternatively, the solution can be used only to such an extent to which the co-gel carrier is capable of absorbing.

If the tungsten compound is in the precursor form, a calcination is performed for the catalyst in which it is heated in the presence of an oxygen-containing gas, e.g. air. The temperature required is generally 300°–800° C. and the reaction time from 15 minutes to 20 hours. The calcination can also occur in the presence of an olefine containing 2–20 carbon atoms.

A solid tungsten catalyst can be in any desired form, such as in the form of balls, granules or agglomerates, when a solid-bed catalyst is used in the metathesis of olefines. If slurry catalyst systems are used, the catalyst is preferably in the form of a fine powder.

The inventive $WO_3/Si$ metathesis catalysts can be applied to the metathesis reactions of olefines in known manner. The metathesis reaction of olefines is typically performed within a temperature range of 250°–500 C., preferably within the range of 380°–130° C. The metathesis reaction is specific for the catalyst system used. A suitable temperature range for the $WO_3/SiO_2$ system is thus within the range of 300°–450° C.

The metathesis is performed by bringing the feeding olefine in either a liquid or gas phase into contact with the inventive catalyst. If the reaction is performed in a liquid phase, suitable solvents or diluents may be used, such as saturated aliphatic hydrocarbons, e.g. pentane, hexane, cyclohexane, etc., or aromatic hydrocarbons, such as benzene or toluene. If the reaction is performed in a gas phase, suitable diluents may be used, such as aliphatic hydrocarbons, e.g. methane, ethane, propane, butane or inert gases, such as nitrogen.

The reaction time is not critical, and it may vary within a wide range. A reaction time from 0.1 seconds to 24 hours is generally sufficient.

The metathesis reaction is typically performed by passing the olefine through a reaction vessel, which is partially or totally packed full with the catalyst. It has been observed according to the invention that the activity and conversion of the catalysts can be essentially improved by diluting the tungsten-containing catalyst with a carrier which contains no tungsten. This may result from the fact that the reaction balance is reached very rapidly in the metathesis reaction. The reaction balance is reached in the catalyst already on its surface layers, whereby the remaining portion of the catalyst can no longer affect the balance position, but is rather in a way, unnecessary. A considerably diluted catalyst can thus be used in the catalyst bed. Thus, in the inventive process, a catalyst bed can be used, which includes a catalyst containing ca. 6% of tungsten, the remaining portion being formed of the inventive carrier prepared by gelling.

The dilution in the catalyst bed can also be achieved so that the tungsten containing catalyst is placed under the carrier layers containing no tungsten or between such layers. The insert layer then acts as a heat compensator and a mixing intensifier.

In the inventive metathesis process there may be converted for example, acyclic mono-olefines, e.g. 1-butene, 2-butene, 1-pentene, 2-pentene, 1-hexane, 1,4-hexadiene, 2-heptane, 1-octane, 2-nonene, 1-dodecene, etc. Propene is especially suitable. In addition thereto, a raffinate to be derived from an MTBE unit may be used as a feed, which raffinate contains various quantities of suitable butenes as well as paraffins which act as diluents. The oxygen containing components have to be removed before the metathesis reaction, since they impede the reaction. For example, an activated alumina, a copper catalyst and molecular sieves can be used for purifying the raffinate feed.

DESCRIPTION OF PREFERRED EMBODIMENTS

The following are examples given to further illustrate the present invention. The scope of the invention is not, however, meant to be limited to the specific details of the examples.

EXAMPLE 1

A metathesis catalyst was prepared by impregnating 1.34 g of a carrier (manufacturer Grace Co.) twice with a 4% $NH_4WO_3$ water solution and by drying the water periodically by heating in an oven at 115° C. This silica titania co-gel is a silica titania carrier prepared by gelling, in which the titania is homogeneously distributed into the whole gel quantity. The gel's titania content was 4.3%, particle size 0.05 mm, surface area 467 $m^2/g$ and pore volume 1.07 ml/g. The catalyst thus obtained was dried at 120° C. overnight. The catalyst was tested in the propene metathesis reaction by loading into a tube reactor a mixture, which contained 0.102 g of the catalyst prepared in the manner described above and 0.718 g of the same carrier without tungsten. The catalyst was activated by passing through the catalyst bed first air at 600° C. at a flow rate of 10 l/h for 1.5 hours and then nitrogen at the same temperature at a flow rate of 10 l/h for 30 minutes.

Thereafter, propene was passed into the reactor at 400° C. first at a flow rate of 1.07 l/h and after 3 hours at a flow rate of 3.5 l/h. The propene then converted into ethene and butanes. The results are shown in Table 1, in which the activities of the catalyst are given as units g of the converted propene/g of $Wo \times h$. The percentages of the product distributions are percents by weight.

TABLE 1

| Time (h) | Ethene (%) | Propene (%) | Butenes (%) | Others (%) | Conversion (%) | Activity (g/gh) |
|---|---|---|---|---|---|---|
| 0 | 10077 | 65.021 | 22.059 | 2.84 | 34.98 | 300.80 |
| 5 | 11.195 | 61.660 | 25.598 | 1.55 | 38.34 | 1078.80 |
| 10 | 11.104 | 61.871 | 25.649 | 1.47 | 38.13 | 1072.54 |
| 20 | 10.529 | 63.550 | 24.726 | 1.20 | 36.45 | 1025.32 |
| 30 | 9.957 | 65.445 | 23.584 | 1.00 | 34.56 | 972.01 |
| 40 | 9.729 | 66.165 | 23.198 | 0.91 | 33.83 | 951.76 |

The metal content of the catalyst was 5.25%.

The reaction was an extremely pure metathesis reaction without acid catalytic side reactions.

EXAMPLE 2

A metathesis catalyst was prepared, as described in Example 1, but as a carrier was used a silica-magnesia co-gel (Manufacturer W.R. Grace), which is a silica-magnesia prepared by gelling, in which the magnesium occurs only as surface ions. The gel's magnesium content was 1.0%, particle size 0.05 mm, surface area 334 $m^2/g$ and pore volume 1.07 ml/g. The catalyst obtained was examined in the propene metathesis reaction by loading into the uppermost portion of a reactor 0.0945 g of pure catalyst and under this layer a mixture, which contained 0.0268 g of the catalyst prepared in the manner described above as well as 0.0707 g of a pure carrier. The tungsten content of the catalyst was 5.8% of the catalyst. The activities of the catalyst was performed as in Example 1.

Thereafter, propene was passed into a reactor at 400° C. first at a flow rate of 3.0 l/h and after 2 hours at a flow rate of 5.0 l/h. The results are shown in Table 2.

TABLE 2

| Time (h) | Ethene (%) | Propene (%) | Butenes (%) | Others (%) | Conversion (%) | Activity (g/gh)² |
|---|---|---|---|---|---|---|
| 0 | 9.921 | 48.985 | 34.597 | 6.50 | 51.02 | 1357.01 |
| 2 | 8.699 | 48.857 | 35.499 | 6.95 | 51.14 | 2267.36 |
| 5 | 9.468 | 51.393 | 37.294 | 1.85 | 48.61 | 2154.93 |
| 10 | 8.868 | 52.600 | 37.460 | 1.07 | 47.40 | 2101.42 |
| 20 | 7.797 | 58.856 | 33.053 | 0.29 | 41.14 | 1824.07 |

As in Example 1, the reaction was an extremely pure metathesis reaction without acid catalytic side reactions.

REFERENCE EXAMPLE 1

A catalyst was prepared in the same way as described in Example 1, but a pure silica was used as a carrier. The tungsten content of the catalyst was 5.8% and 0.3782 g of this catalyst was used in the catalyst bed. The activation was performed by passing air through the bed air at 600° C. for 90 minutes.

The metathesis reaction of propene was examined in the presence of this catalyst according to Example 1. The results are shown in Table 3.

TABLE 3

| Time (h) | Ethene (%) | Propene (%) | Butenes (%) | Others (%) | Conversion (%) | Activity (g/gh) |
|---|---|---|---|---|---|---|
| 1 | 7.877 | 46.435 | 34.533 | 11.155 | 53.565 | 33.71* |
| 20 | 7.860 | 50.782 | 39.982 | 1.376 | 49.218 | 93.85** |
| 25 | 8.101 | 51.418 | 39.366 | 1.115 | 48.582 | 123.52*** |
| 29 | 7.407 | 54.803 | 36.863 | 0.927 | 45.197 | 173.50**** |

Note! The propene flows:
*1.0 l/h
**3.03 l/h
***4.04 l/h
****6.1 l/h

COMPARISON EXAMPLE 2

A metathesis catalyst was prepared, as described in Example 1, but PQ's silica CS-1231 was used as a carrier. Particle size of the silica was 0.6–1.6 mm and the surface area 330 m²/g. The carrier was impregnated twice with a 4% NH$_4$WO$_3$ water solution. After the drying, the catalyst was still sieved with an 0.5 mm sieve and the fine portion was rejected. The W content of the coarse portion used as catalyst was 5.8%.

MgO sieved with an 0.5 mm sieve and comprising 1.5% of the weight was mixed mechanically into the catalyst described above and packed by layers into the reactor such that 0.1064 g of the carrier and 0.1025 g of the catalyst were placed first and finally 0.1026 g of the carrier.

The activation of the catalyst was performed as in Example 1. The results are shown in Table 4.

TABLE 4

| Time (h) | Ethene (%) | Propene (%) | Butenes (%) | Others (%) | Conversion (%) | Activity (g/gh) |
|---|---|---|---|---|---|---|
| 1 | 10.06 | 44.81 | 31.39 | 13.19 | 55.19 | 135.98* |
| 3 | 9.35 | 48.19 | 34.52 | 7.86 | 51.81 | 370.78** |
| 10 | 8.44 | 51.35 | 37.06 | 3.06 | 48.65 | 348.17 |
| 23 | 5.63 | 68.20 | 25.92 | 0.24 | 31.80 | 378.29*** |

Note! The propene feeds:
*1.05 l/h
**3.05 l/h
***5.07 l/h

EXAMPLE 3

As in Example 1, a tungsten catalyst was prepared for an SiO$_2$-MgO carrier in this example, the metal content of which catalyst was 6.03%. In the example, a larger reactor was used, into which a larger quantity of the catalyst could be loaded, and ethene and t-and c-butenes were used as feeds. The feeding ratios could be adjusted within a relatively large range for examining the properties of the catalyst. When loading the catalyst, an insert silicon carbide was now used as a diluent instead of a pure carrier. Starting from the top portion of the reactor, 1.0 g of SiC, 0.5 g of the catalyst and 5.06 g of SiC were packed into the reactor. The catalyst was calcinated, as in Example 1. Table 5 shows the results of the run. The temperature of the reactor was maintained at 400° C. during the entire run.

TABLE 5

| Time (h) | Ethene (%) | Propene (%) | t-butene (%) | c-butene (%) | Others (%) | Met. act (g/gmet *h) | Conv. g/gh |
|---|---|---|---|---|---|---|---|
| 5 | 16.06 | 30.00 | 32.79 | 8.59 | 9.55 | 278.0 | 35.50* |
| 60 | 13.10 | 51.31 | 21.10 | 12.74 | 0.61 | 475.5 | 49.17* |
| 125 | 14.74 | 48.12 | 23.33 | 22.29 | 0.51 | 445.9 | 46.78** |
| 190 | 11.79 | 50.85 | 18.41 | 17.36 | 0.59 | 471.2 | 46.46** |
| 370 | 12.89 | 46.54 | 17.34 | 22.35 | 0.22 | 418.3 | 40.19*** |
| 406 | 13.09 | 44.83 | 16.75 | 24.51 | 0.82 | 403.0 | 38.9*** |

Note! The Table uses standard-run values, with return after each change
Feeds:
*ethene 7.60 and t-butene 8.2 l/h
**ethene 7.60 and c-butene 8.2 l/h

EXAMPLE 4

The Example was performed according to Example 3, and also the catalyst load was similar. As a feed was now used Neste's own raffinate (OLEFJK), which according to the product specification contains ca 50% of butenes and 8% of 1-butene, which are metathesis active, was used. For removing the impurities, MeOH, MTBE, dimethyl ether and isobutene, in the olefine fraction, the feed was provided with an efficient purification system.

In this connection, also the reactor temperature was varied.

TABLE 6

| Time (h) | Ethene (%) | Propene (%) | t-butene (%) | c-butene (%) | Others (%) | Met. act (g/gmet *h) | Conv. g/gh |
|---|---|---|---|---|---|---|---|
| 4.5* | 51.41 | 13.43 | 8.40 | 3.35 | 0.00 | 151.1 | 26.30 |
| 65.5 | 46.74 | 28.54 | 2.40 | 1.26 | 0.40 | 320.9 | 64.51 |
| 223.5 | 46.43 | 30.92 | 2.30 | 1.37 | 0.44 | 347.7 | 63.83 |

Note! The Table shows only a standard-level stability after the changes. The catalyst is extremely stable and requires no regeneration.

Feeds: ethene 17.66 l/h and raff II 7.24 l/h.

While the invention has been illustrated with respect to particular metathesis reactions for the convertion of olefines, it is apparent that variations and modifications of the invention can be made without departing from the spirit or the scope of the invention.

What is claimed is:

1. A metathesis process for the conversion of olefines, which comprises bringing at least one olefine into contact with a solid catalyst system comprising between about 0.1-40% by weight of a tungsten compound on a solid silica carrier, under such reaction conditions that said catalyst system converts the olefines into olefines of a different molecular weight, said silica carrier being a magnesium oxide or titanium oxide-containing co-gel prepared by means of a co-gelling system.

2. The metathesis process according to claim 1, wherein said carrier contains at least 80% of silica and not more than 20% of magnesium oxide.

3. The metathesis process according to claim 1, wherein in that said carrier contains at least 80% of silica and not more than 20% of titanium oxide.

4. The process according to claim 1, wherein said catalyst system comprises a catalyst bed which contains said silica carrier, which does not contain tungsten or an inert medium other than silica, together with said tungsten-containing carrier.

5. The process according to claim 1, wherein said catalyst system comprises a catalyst bed having, in the direction of feed flow, an upper layer comprising said silica carrier, which does not contain tungsten or an inert medium other than silica, and a lower layer comprising a tungsten-containing carrier.

6. The process according to claim 1, wherein said olefine comprises one or more olefines containing 2-20 carbon atoms.

7. The process according to claim 6, wherein said olefine mixture contains up to 80% of i- or n-paraffins.

8. The metathesis process according to claim 1, wherein the metathesis reaction is performed at a temperature of 380°-430° C. and at a pressure of not more than 15 bar.

9. The process according to claim 2 wherein said catalyst system comprises a catalyst bed, which contains said silica carrier, which does not contain tungsten or an insert medium other than silica together with said tungsten-containing carrier.

10. The process according to claim 3, wherein said catalyst system comprises a catalyst bed, which contains said silica carrier, which does not contain tungsten or an inert medium other than silica, together with said tungsten-containing carrier.

11. The process according to claim 4 wherein said catalyst system comprises a catalyst bed having, in the direction of feed flow, an upper layer comprising said silica carrier, which does not contain tungsten or an inert medium other than silica, and a lower layer comprising a tungsten-containing carrier.

* * * * *